US007087431B2

(12) United States Patent
Wu et al.

(10) Patent No.: US 7,087,431 B2
(45) Date of Patent: Aug. 8, 2006

(54) EX VIVO GENERATION OF FUNCTIONAL LEUKEMIA CELLS IN A THREE-DIMENSIONAL BIOREACTOR

(75) Inventors: J. H. David Wu, Pittsford, NY (US); Athanassios Mantalaris, Middlesex (GB); Nicki Panoskaltsis, Middlesex (GB)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/796,830

(22) Filed: Mar. 1, 2001

(65) Prior Publication Data
US 2001/0034026 A1    Oct. 25, 2001

Related U.S. Application Data

(60) Provisional application No. 60/186,564, filed on Mar. 2, 2000.

(51) Int. Cl.
C12N 5/06      (2006.01)
(52) U.S. Cl. .................. 435/395; 435/399; 435/375; 435/383; 435/385
(58) Field of Classification Search .............. 435/41, 435/325, 395, 399, 375, 383, 385; 424/93.1, 424/277.1
See application file for complete search history.

(56) References Cited

U.S. PATENT DOCUMENTS

| | | | |
|---|---|---|---|
| 5,459,069 | A | 10/1995 | Palsson et al. |
| 5,478,739 | A | 12/1995 | Slivka et al. |
| 5,496,722 | A | 3/1996 | Goodwin et al. |
| 5,512,480 | A | 4/1996 | Sandstrom et al. |
| 5,541,107 | A | 7/1996 | Naughton et al. |
| 5,578,485 | A | 11/1996 | Naughton et al. |
| 5,719,058 | A | 2/1998 | Rodan et al. |
| 5,827,729 | A | 10/1998 | Naughton et al. |
| 5,830,708 | A | 11/1998 | Naughton |
| 5,855,608 | A | 1/1999 | Brekke et al. |
| 5,856,186 | A | 1/1999 | Rodan et al. |
| 6,093,533 | A | 7/2000 | Rodan et al. |

FOREIGN PATENT DOCUMENTS

| | | |
|---|---|---|
| JP | 5-192178 | 8/1993 |
| JP | 6-46877 | 2/1994 |
| JP | 9-59174 | 3/1997 |
| JP | 11-9269 | 1/1999 |
| WO | WO 87/06120 | 10/1987 |
| WO | WO 93/07271 | 4/1993 |
| WO | WO 01/12785 | 2/2001 |

OTHER PUBLICATIONS

Vunjak-Novakovi, et al. Biotechnol Prog. 1998, 14:193-202.*
Rummel, et al., 1994, J Hematother, 3(3):213-8.*
Liu, et al, 1991, Cytotehcnology, 5(2):129-39.*
Visani, et al. 1994, Leukemia, 8(12):2183-87.*
Tsunogake, et al., 1991, Int J Immunotherapy, 7(2):63-72.*
Jiang et al (Aug. 1, 1998, Blood, vol. 92, pp. 834-841).*
Vassiliadis (1994, Haematologia, vol. 26, pp. 29-37,abstract only).*
Eaves et al (1993, Leuk Lymphoma, vol. 11, Suppl 1, pp. 259-263, abstract only).*
Merriam-Webster Online Dictionary downloaded from URL > m-w.com on Jul. 24, 2003.*
Vassiliadis (1994, Haematologia, vol. 26, pp. 29-37, entire article with this Action).*
Lange (1989, Cell growth and division, a practical approach, Baserga, R. ed., IRL Press, Chapter 4, pp. 61-76.*
Chen et al (1997, Biochim Biophys Acta, vol. 1358, pp. 200-208, abstract only).*
Merriam-Webster Online Dictionary (down loaded from url>>m-w.com on Mar. 21, 2004) for semisynthetic.*
Definition of "particle" in Merriam-Webster Online dictionary downloaded from URL>>www.m-w.com on Nov. 21, 2004, p. 1 only of 2.*
Definition of "porous" in Merriam-Webster Online dictionary downloaded from URL>>www.m-w.com on Nov. 21, 2004, p. 1 only of 2.*
Gloeckner et al., "Hollow-Fiber Bioreactor System for the Expansion of Activated Human T-Cells in High Densities," *Blood* 96(11)(Part 1):776a (2000) (abstract only).
Visani et al., All-trans Retinoic Acid Potentiates Megakaryocyte Colony Formation: *In Vitro* and *In Vivo* Effects After Administration to Acute Promyelocytic Leukemia Patients, *Leukemia* 8(12):2183-2187 (1994).
Schwarzmeier et al., "Myelosuppression in HCL: Role of Hairy Cells, T Cells and Haematopoietic Growth Factors," *Eur. J. Heamatology* 52(5):257-262 (1994).
Tsunogake et al., "Differential Effects of Ubenimex on Growth of Normal Human Haematopoietic Progenitors and Leukaemic Cells *In Vitro*," *International Journal Immunotherapy* 7(2):63-72 (1991).
Applebaum, F.R., "Molecular Diagnosis and Clinical Decisions in Adult Acute Leukemia," *Seminars in Hematology* 36(4):401-410 (1999).

(Continued)

Primary Examiner—Misook Yu
(74) Attorney, Agent, or Firm—Nixon Peabody LLP

(57) ABSTRACT

The present invention provides cultured leukemia cells. The method comprises isolating mononuclear cells, which contain leukemia cells, culturing the leukemia cells in a chamber having a scaffolding covered or surrounded with culture medium, where the scaffolding allows for leukemia cells to have cell to cell contacts in three dimensions. The subject leukemia cells are useful for screening compounds which inhibit or stimulate leukemia cell function or formation.

33 Claims, 14 Drawing Sheets

OTHER PUBLICATIONS

Lange, B.J., "Growth of Human Leukaemia Cells *in vitro*," in *Cell Growth and Division—A Practical Approach*, Chapter 4, Baserga, Renato, ed., Oxford, NY: IRL Press at Oxford University Press, pp. 61-79 (1989).

Naughton et al., "A Three-Dimensional Culture System for the Growth of Hema-Topoietic Cells," *Bone Marrow Purging and Processing* 333:435-445 (1990).

Naughton et al., "Hematopoiesis on Suspended Nylon Screen-Stromal Cell Microenvironments," *Journal of Biomechanical Engineering* 113:171-177 (1991).

Tjota et al., "Stromal Cells Derived from Spleen or Bone Marrow Support the Proliferation of Rat Natural Killer Cells in Long-Term Culture," *Proc. Soc. Exp. Biol. Med.* 200(3):431-441 (1992).

Naughton et al., "Differential Effects of Drugs Upon Hematopoiesis Can Be Assessed in Long-Term Bone Marrow Cultures Established on Nylon Screens," *Proc. Soc. Exp. Biol. Med.* 199(4):481-90 (1992).

Naughton et al., "Hematopoiesis on Nylon Mesh Templates. Comparative Long-Term Bone Marrow Culture and the Influence of Stromal Support Cells," *Ann. N.Y. Acad. Sci.* 554:125-40 (1989).

Naughton et al., "Hematopoiesis on Nylon Mesh Templates. I. Long-Term Culture of Rat Bone Marrow Cells," *Journal of Medicine*, 18(3, 4):219-250 (1987).

Benayahu et al., "Mineralization of Marrow-Stromal Osteoblasts MBA-15 on Three-Dimensional Carriers," *Calcif. Tissue Int.* 55:120-127 (1994).

Ishaug et al., "Bone Formation by Three-Dimensional Stromal Osteoblast Culture in Biodegradable Polymer Scaffolds," *J. Biomed. Materials Res.* 36:17-28 (1997).

Rosenzweig et al., "Enhanced Maintenance and Retroviral Transduction of Primitive Hematopoietic Progenitor Cells Using a Novel Three-Dimensional Culture System," *Gene Therapy* 4:928-936 (1997).

Salisbury et al., "Three-Dimensional Reconstruction of Non-Hodgkin's Lymphoma in Bone Marrow Trephines," *J. Pathol.* 181:451-454 (1997).

Glowacki et al., "Perfusion Enhances Functions of Bone Marrow Stromal Cells in Three-Dimensional Culture," *Cell Transplantation*, 7(3):319-326 (1998).

Martin et al., "*In Vitro* Differentiation of Chick Embryo Bone Marrow Stromal Cells into Cartilaginous and Bone-Like Tissues," *J. Orthopaedic Res.* 16:181-189 (1998).

Bagley et al., "Extended Culture of Multipotent Hematopoietic Progenitors Without Cytokine Augmentation in a Novel Three-Dimensional Device," *Experi. Hematology* 27(3):496-504 (1999).

Dexter et al., "Proliferation of Haemopoietic Stem Cells *In Vitro*," *Brit. J. Haematol.* 28:525-530 (1974).

Fluckiger et al., "*In Vitro* Reconstitution of Human B-Cell Ontogeny: From CD34+ Multipotent Progenitors to IG-Secreting Cells," *Blood* 92(12):4509-4520 (1998).

Mantalaris et al., "Engineering a Human Bone Marrow Model: A Case Study on *Ex Vivo* Erythropoiesis," *Biotechnology Progress* 14(1):126-133 (1998).

Poznansky et al., "Efficient Generation of Human T Cells from a Tissue-Engineered Thymic Organoid," *Nature Biotechnology* 18(7):729-734 (2000).

Pollack, S.B., "Production and Differentiation of NK Lineage Cells in Bone Marrow," *Nat. Immun.* 12:177-193 (1993).

Porter et al., "A Tissue of T Cells," *Nature Biotechnology* 18(7):714-715 (2000).

Slovick et al., "Survival of Granulocytic Progenitors in the Nonadherent and the Adherent Compartments of Human Long-Term Bone Marrow Cultures," *Experimental Hematology* 12:327-338 (1984).

Wang et al., "Multilineal Hematopoiesis in a Three-Dimensional Murine Long-Term Bone Marrow Culture," *Experimental Hematology* 23:26-32 (1995).

Whitlock et al., "Murine B Cell Lymphopoiesis in Long Term Culture," *J. Immunological Methods* 67:353-369 (1984).

Whitlock et al., "Long-Term Culture of B Lymphocytes and Their Precursors from Murine Bone Marrow," *Proc. Natl. Acad. Sci USA* 79:3608-3612 (1982).

Flanagan, A.M., "An Assessment of the Ability of Human Bone Marrow Cultures to Generate Osteoclasts," *Int. J. Exp. Path.* 73:387-401 (1992).

Helfrich et al., "Osteoclast Generation From Human Fetal Bone Marrow in Cocultures with Murine Fetal Long Bones," *Cell and Tissue Research* 249(1):125-136 (1987).

Horton et al., "Cell Surface Characterization of the Human Osteoclast: Phenotypic Relationship to Other Bone Marrow-Derived Cell Types," *J. Pathol.* 144:281-294 (1984).

Kukita et al., "Osteoclast-Like Cells Formed In Long-Term Human Bone Marrow Cultures Express a Similar Surface Phenotype As Authentic Osteoclasts," *Laboratory Investigation* 60(4):532-538 (1989).

Lambrecht et al., "Human Osteoclast-Like Cells in Primary Culture," *Clinical Anatomy* 9(1):41-45 (1996).

Matsuzaki et al., "Osteoclast Differentiation Factor (ODF) Induces Osteoclast-Like Cell Formation in Human Peripheral Blood Mononuclear Cell Cultures," *Biochemical and Biophysical Research Communications* 246:199-204 (1998).

Mizuno et al., "Severe Osteoporosis in Mice Lacking Osteoclastogenesis Inhibitory Factor/Osteoprotegerin," *Biochemical and Biophysical Research Communications* 247:610-615 (1998).

Nesbitt et al., "Trafficking of Matrix Collagens Through Bone-Resorbing Osteoclasts," *Science* 276:266-269 (1997).

Takahashi etal., "Osteoclast-Like Cells Form in Long-Term Human Bone Marrow But Not in Peripheral Blood Cultures," *The Journal of Clinical Investigation, Inc.* 83:543-550 (1989).

Thavarajah et al., "$1,25(OH)_2D_3$ and Calcipotriol (MC903) Have Similar Effects on the Induction of Osteoclast-Like Cell Formation in Human Bone Marrow Cultures," *Biochemical and Biophysical Research Communications* 171(3):1056-1063 (1990).

Thavarajah et al., "$1,25(OH)_2D_3$ Induces Differentiation of Osteoclast-Like Cells From Human Bone Marrow Cultures," *Biochemical and Biophysical Research Communications* 176(3):1189-1195 (1991).

Tsukii et al., "Osteoclast Differentiation Factor Mediates an Essential Signal for Bone Resorption Induced by $1\alpha,25$-Dihydroxyvitamin D3, Prostaglandin E2, or Parathyroid Hormone in the Microenvironment of Bone," *Biochemical and Biophysical Research Communications* 246:337-341 (1998).

Hakeda et al., "The Growth and Culture of Bone Cells: Osteoclastic," *Principles of Bone Biology* pp. 1217-1228 (1996).

Eaves et al., "Methodology of Long-Term Culture of Human Hemopoietic Cells," *J. Tiss. Cult. Meth.* 13:55-62 (1991).

Koller et al., "Large-Scale Expansion of Human Stem and Progenitor Cells from Bone Marrow Mononuclear Cells in Continuous Perfusion Cultures," *Blood* 82(2):378-384 (1993).

Coligan et al., eds., "Current Protocols in Immunology", vol. 1, Chapter 3, sections II, III, and IV, Chapter 7, section IV and Chapter 12 (1995).

Schölzel et al., "Stimulation of Proliferation and Differentiation of Acute Myeloid Leukemia Cells on a Bone Marrow Stroma in Culture," *Exp. Hematol.*, 13:664-669 (1985).

Wang et al., "A Novel Three-Dimensional Long-Term Bone Marrow Bioreactor Culture System," *Animal Cell Technology: Basic & Applied Aspects*, 115-120 (1994).

Marie et al., "In vitro Sensitivity of Leukemic Clonogenic Cells to Four Anthracyclines (Adriamycin, Daunorubicin, Rubidazone and Aclacinomycin) in Human Acute Myeloid Leukemia," *Nouv. Rev. Fr. Hematol.*, 27:163-167 (1985).

* cited by examiner (wk 2.3)

(wk 2.3)

(wk 2.3)

(wk 2.3)

EX VIVO GENERATION OF FUNCTIONAL LEUKEMIA CELLS IN A THREE-DIMENSIONAL BIOREACTOR

This application was originally filed as U.S. Provisional Application Ser. No. 60/186,564 on Mar. 2, 2000.

The invention described herein was made with United States Government support under National Science Foundation contract number BES-963160 and may therefore be subject to certain rights of the U.S. government.

FIELD OF THE INVENTION

The present invention relates to the field of cell culture and, in particular, to methodologies and compositions related to cultured leukemia cells.

BACKGROUND OF THE INVENTION

Leukemia is a form of cancer that begins in the blood-forming cells of the bone marrow—soft, inner part of the bones. Leukemia—which literally means "white blood" in Greek—occurs when there is an excess of abnormal white blood cells in the blood. Known as leukocytes, these cells are so plentiful in some individuals that the blood actually has a whitish tinge.

Under normal circumstances, the blood-forming, or hematopoietic, cells of the bone marrow make leukocytes to defend the body against infectious organisms such as viruses and bacteria. But if some leukocytes are damaged and remain in an immature form, they become poor infection fighters that multiply excessively and do not die off as they should. The leukemic cells accumulate and lessen the production of oxygen-carrying red blood cells (eythrocytes), blood-clotting cells (platelets), and normal leukocytes. If untreated, the surplus leukemic cells overwhelm the bone marrow, enter the bloodstream, and eventually invade other parts of the body, such as the lymph nodes, spleen, liver, and central nervous system (i.e. brain, spinal cord). In this way, the behavior of leukemia is different than that of other cancers, which usually begin in solid organs and may spread to the bone marrow.

There are more than a dozen varieties of leukemia, but the following four types are the most common: acute lymphocytic leukemia (ALL); acute myelogenous leukemia (AML); chronic lymphocytic leukemia (CLL); and chronic myelogenous leukemia (CML).

Acute leukemias usually develop suddenly, whereas some chronic varieties may exist for years before they are diagnosed.

Leukemia often is thought to be a childhood disease. In fact, leukemia strikes 10 times as many adults as children. The American Cancer Society predicted that about 30,200 new leukemia cases—27,900 adults and 2,300 children—would be diagnosed in the United States during 1999. Acute myelogenous leukemia (AML) is the most frequently reported form of acute leukemia in adults, and approximately 10,100 new cases were anticipated in 1999.

About 41% of the 30,200 latest cases will have chronic leukemia—an estimated 7,800 chronic lymphocytic leukemia (CLL) cases and 4,500 chronic myelogenous leukemia (CML) cases. In addition, hairy cell leukemia (HCL), a slow-growing lymphocytic cancer, will account for about 604 cases (2% of all leukemias). Sadly, it was estimated that approximately 22,100 American adults and children would die of leukemia in 1999.

Acute myelogenous leukemia (AML) is the most common adult form of leukemia, affecting nearly 5 in every 100,000 men each year.

Chronic leukemia, like many other cancers, is a "disease of old age." The average age of individuals with chronic lymphocytic leukemia (CLL) is roughly 70 years, and the average age of chronic myelogenous leukemia (CML) patients is 40 to 50 years. By contrast, acute lymphocytic leukemia (ALL) is largely a pediatric disease, usually appearing in children who are under 10 years of age.

In general, leukemia affects more men than women throughout the world, although the male:female ratio is highest in CLL patients in Western countries.

In view of leukemia's prevalence as a disease, the need remains for new ways to treat leukemia. As a result, development of an in vitro culture system of leukemic cells that closely approximates the environment found in vivo becomes important. While in vivo leukemic cells enjoy a selective growth advantage over normal haematopoietic cells in leukemic patients, the opposite occurs in vitro.

Murine models are used to study leukemias and the impact of different therapies on the disease. However, differences in physiology between mice and humans render the murine models as inadequate.

Leukemic cells are so difficult to grow and maintain that failure to form any colonies in vitro is a characteristic by which some myeloid leukemias are classified; normal cells have the selective growth advantage in vitro. This advantage is demonstrated by failure to establish long-term Dexter-type suspension cultures of cells of patients with Philadelphia chromosome ($Ph^1$) positive chronic myeloid leukemia. Over a period of weeks or months the number of cells with the $Ph^1$ karotype decreases until it is undetectable and the number of normal mitoses increases to 100%. The relative inability to survive in vitro under these conditions is now being exploited to purge human marrow of residual leukemic cells in order to return it to the patient some days later in the form of a leukemia-free autologous marrow transplant. The cells transplanted are cultured under the conditions that deviates from the bone marrow environment, because the Dexter culture supports cell growth only in two-dimensions.

Despite the propensity for normal cells to outgrow leukemic cells in vitro or for the leukemic cells to die, several methods for growing leukemic cells in short-term culture have been developed. The method most often used involves leukemic colony-formation in soft agar or methylcellulose. The techniques for growing leukemic colonies were first adopted from systems for normal haematopoietic colony-forming progenitors in semi-solid media and then modified to the particular requirements of leukemic cells. Most studies of leukemic colony-formation deal with acute non-lymphoblastic leukemic (ANLL) cells, the prototype leukemic colony assay. Leukemic cells can be obtained from peripheral blood, bone marrow aspirate or biopsy or rarely from a chloroma or spleen. The procedure for preparing leukemic cells for culture entails removal of the acidic heparin which may harm the cells, removal of the patient's serum which may inhibit growth, removal of erythrocytes which make it difficult to see the leukemic cells, and removal of cells which may inhibit leukemic growth such as granulocytes. Sometimes, cells which may stimulate growth, (e.g., T-lymphocytes and monocytes) or which may themselves form colonies that are difficult to distinguish from leukemic colonies are removed.

The second method for growing leukemic cells is in a suspension culture. Most leukemic cells survive for only a few days in culture media with fetal calf serum.

Finally, a third method to support growth of leukemic cells is the xenografting of human cells into sites such as the anterior chamber of the eye of the nude mouse.

It is now apparent that growth of haematopoietic cells and of leukemic cells in vitro and in vivo is the result of complex interactions between colony-stimulating factors, growth factors, and growth factor receptors. These factors may be humoral factors present in vivo in plasma; they may be autocrine factors generated by the leukemic cells themselves and may be paracrine factors that are dependent on cell-to-cell interactions in the haematopoietic microenvironment.

The establishment of long-term bone marrow cell cultures have been attempted using a pre-established stromal cell support matrix where the stromal matrix provides the support, growth factors, and regulatory factors necessary to sustain long-term active proliferation of cells in culture (Naughton et al., "Hematopoiesis on Suspended Nylon Screen-Stromal Cell Microenvironments," *J. Biomech. Eng.*, 113:171–177 (1991)). This is based, in part, on the discovery that growth of stromal cells on a nylon screen template will sustain active proliferation of cells in culture for longer periods of time than will monolayer systems. The screen template is a planar, essentially two-dimensional matrix having minimal depth which is defined by the thickness of the strands of nylon mesh.

There has been a lack of a consistent cell culture system for growing leukemia cells. A long-term leukemia cell culture system is needed for characterizing the leukemic progenitors, defining molecules that regulate leukemic proliferation and differentiation, and screening potential chemotherapeutic agents.

The present invention is directed to overcoming the deficiencies in the art.

SUMMARY OF THE INVENTION

The present invention provides methods for culturing leukemia cells. The method comprises isolating mononuclear cells, which contain leukemia cells and culturing the cells in a chamber having a scaffolding covered or surrounded with culture medium. The scaffolding allows for the cells to have cell to cell contacts in three dimensions. Optionally, the culture medium can be reseeded with leukemia cells. This procedure can also be used for generating leukemia cells.

The present invention also provides a method of screening for drugs for efficacy in treating leukemia on an individual basis. The method comprises isolating mononuclear cells, which contain leukemia cells, culturing the cells in a container having a scaffolding covered or surrounded with culture medium, where the scaffolding allows for cells to have cell to cell contacts in three dimensions, adding a test compound to the container, and determining whether the test compound inhibits growth of leukemia cells. The test compound may be a single compound, a series or a combination of compounds, with different testing dosages and/or durations. The present invention also includes treating the leukemia patient with the compound which has been determined to inhibit leukemia cells in the test.

The present invention further relates to a method of identifying genes which are related to leukemia cell formation or function. The method comprises isolating mononuclear cells, which contain leukemia cells, culturing the leukemia cells in a chamber having a scaffolding covered or surrounded with culture medium, where said scaffolding allows for cells to have cell to cell contacts in three dimensions, altering one or more culture conditions in a test culture, determining a leukemia cell number and function in the test sample, and screening for a gene or genes associated with the change in leukemia cell number or function in the test sample. Genes may be screened using many different well known methods such as differential gene display, RNA arbitrarily primed (RAP)-PCR, or gene microarray analysis. Gene screening can also be carried out by comparing gene expression between the culture method of the present invention, which support 3-D cell growth, and the traditional 2-D Dexter culture, which does not support leukemia cells.

The present invention also provides a method for screening for compounds which effect leukemia cell formation. The method comprises isolating mononuclear cells which contain leukemia cells, culturing the cells in a container having a scaffolding covered or surrounded with culture medium where the scaffolding allows for leukemia cells to have cell to cell contacts in three dimensions, adding a test compound to the container, removing cultured cells, and determining the ability of a test compound to effect leukemia cell formation.

The present invention also provides a method for diagnosis or prognosis of leukemia. The method comprises isolating mononuclear cells which possibly contain leukemia cells, culturing the cells in a container having a scaffolding covered or surrounded with culture medium where the scaffolding allows for cells to have cell to cell contacts in three dimensions and leukemia cell formation, and determining the type and the stage of leukemia.

The cell culture technique of the present invention is capable of a culturing human leukemic cells. This has not been possible with prior art systems. As a result, the cell culture system of the present invention is useful in understanding the diseases process, screening potential therapeutics, and elucidating the cause of leukemia. Accordingly, the present invention constitutes a major advance in the art.

DETAILED DESCRIPTION OF THE INVENTION

Figure 1A:
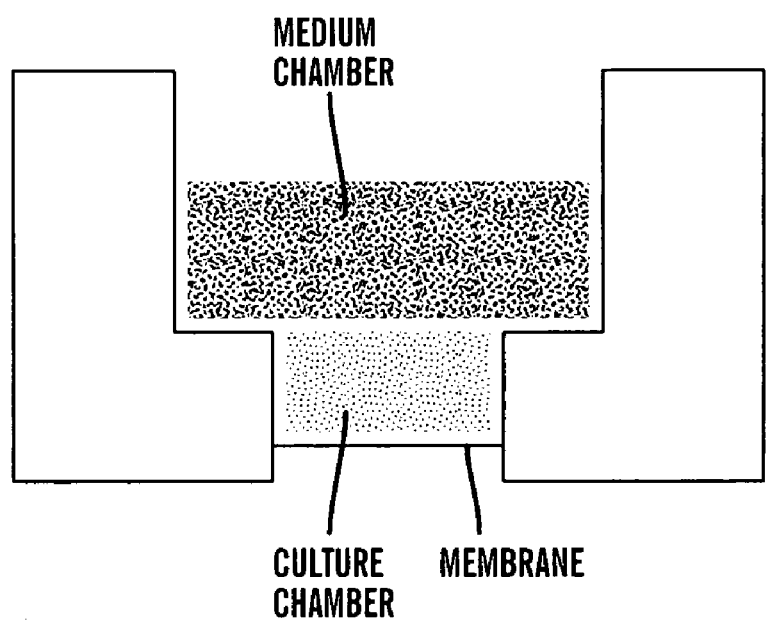
FIG. 1A is a schematic drawing of one possible configuration of a bioreactor. In the configuration pictured here, the porous or fibrous scaffolding is located in the culture chamber.

The present invention is directed to a method of culturing leukemia cells. The method comprises isolating mononuclear cells, which contain leukemia cells and culturing such cells in a chamber having a scaffolding covered or surrounded in culture medium where the scaffolding allows for the leukemia cells to have cell to cell contacts in three dimensions.

The present invention also provides a method for screening for compounds which effect leukemia cell formation. The method comprises isolating mononuclear cells which contain leukemia cells, culturing the cells in a container having a scaffolding covered or surrounded with culture medium where the scaffolding allows for leukemia cells to have cell to cell contacts in three dimensions, adding a test compound to the container, removing cultured cells, and determining the ability of a test compound to effect leukemia cell formation.

The present invention also provides a method for diagnosis or prognosis of leukemia. The method comprises isolating mononuclear cells which possibly contain leukemia cells, culturing the cells in a container having a scaffolding covered or surrounded with culture medium where the scaffolding allows for cells to have cell to cell contacts in three dimensions and leukemia cell formation, and determining the type and the stage of leukemia.

As used herein, the term "leukemia cells" means abnormal cells of the bone marrow and lymphoid tissues and may include, e.g., acute myelocytic leukemia cells, chronic lymphocytic leukemia cells. Acute myelocytic leukemia cells are abnormal cells of the bone marrow of the myeloid lineage arrested at an early stage of maturation. Chronic lymphocytic leukemia cells are abnormal cells of the bone marrow and lymphoid tissues of the lymphocyte lineage arrested at a mature stage of development. The mononuclear cells may be isolated from many different sources such as bone marrow aspirate or biopsy, chloroma, or spleen, peripheral blood, infiltrated organs, tissues, and body fluids, cord blood, fetal liver, and cell lines. The leukemia cells are preferably mammalian leukemia cells. In a more preferred embodiment, the mammalian leukemia cells are human leukemia cells.

In accordance with the present invention, a bioreactor system and method for generating functional leukemia cells is provided. As used herein, "functional leukemia cells" mean leukemia cells which function to sustain the leukemic state (i.e. they do not mature in culture but remain viable and behave as they would in the human host). The bioreactor of the present invention provides a three-dimensional structure which mimics the natural extracellular matrix and ample surface area of the leukemia cells and allows cell to cell interaction at a tissue-like cell density. It is understood that the bioreactor of the present invention may have many different configurations so long as it provides a three-dimensional structure. With respect to the bioreactor, the term "three-dimensional structure" is used interchangeably with the term "scaffolding".

The bioreactor for use in generating functional leukemia cells comprises a container or vessel having at least one chamber or section with scaffolding located therein. The scaffolding for use in the chamber or container may consist of tangled fibers, porous particles, or a sponge-like material. The scaffolding may be formed from a material selected from the group consisting of a synthetic polymer, a natural substance, and a semisynthetic material and may be degradable or non-degradable. Culture media is placed over or around the porous or fibrous substrate.

FIG. 1A illustrates one possible configuration of a bioreactor which may be used to generate functional leukemia cells. In FIG. 1, the porous or fibrous scaffolding is located in a lower, culture chamber. It is understood that the bioreactor of the present invention may have any number of configurations so long as it provides a three dimensional structure (scaffolding).

The walls of the container or vessel may comprise any number of materials such as glass, ceramic, plastic, polycarbonate, vinyl, polyvinyl chloride (PVC), metal, etc. Culture medium which will support the growth and differentiation of hemopoietic and/or accessory cells into functional leukemia cells is placed over and/or around the porous or fibrous material.

Many different porous or fibrous materials may be used as scaffolding in the bioreactor such as, e.g., tangled fibers, porous particles, sponge, or sponge-like material. The porous or fibrous scaffolding allows leukemia cells to lodge onto, proliferate and, if needed, differentiate. For purposes of example only and not limitation, suitable scaffolding substrates may be prepared using a wide variety of materials including natural polymers such as polysaccharides and fibrous proteins, synthetic polymers such as polyamides (nylon), polyesters, polyurethanes and minerals including ceramics and metals, coral, gelatin, polyacrylamide, cotton, glass fiber, corrageenans, and dextrans. Examples of tangled fibers include glass wool, steel wool, and wire or fibrous mesh.

Examples of porous particles include, e.g., beads (glass, plastic, or the like) cellulose, agar, hydroxyapatite, treated or untreated bone, collagen, gels such as Sephacryl, Sephadex, Sepharose, agarose or polyacrylamide. "Treated" bone may be subjected to different chemicals such as, acid or alkali solutions. Such treatment alters the porosity of bone. If desired, the substrate may be coated with an extracellular matrix or matrices, such as, collagen, matrigel, fibronectin, heparin sulfate, hyalumonic and chondroitin sulfate, laminin, hemonectin, or proteoglycans.

The fibrous or porous material used as scaffolding in the bioreactor forms openings or pores into which leukemia cells enter. Once entered, the cells become entrapped or adhered to the fibrous or porous material and colonize and/or aggregate thereon. Cell attachment and colonization can occur merely by inoculating the cells into the culture medium which overlays and/or surrounds the porous or fibrous substrate. Cell attachment and colonization may also occur by inoculating the cells directly onto the porous or fibrous substrates.

In accordance with the present invention, leukemia cells must be able to enter the openings (pores) of the fibrous or porous material. The skilled artisan is cognizant of the different sizes of leukemia cells and, therefore, the pore size needed to accommodate such cells. Generally speaking, a pore size in the range of from about 15 microns to about 1000 microns may be used. Preferably, a pore size in the range of from about 100 microns to about 300 microns is used.

In a preferred embodiment, a membrane is placed in the bioreactor in order to facilitate gas exchange. The membrane is gas permeable and may have a thickness in the range of from about 10 to about 100 μm. In a more preferred embodiment, the membrane has a thickness of about 50 μm. The membrane is placed over an opening in the bottom or side of the chamber or container. In order to prevent excessive leakage of media and cells from the bioreactor, a gasket may be placed around the opening and/or a solid plate placed under or alongside the opening and the assembly fastened.

The cell medium used in the bioreactor may be any of the widely known media used to support growth and differentiation of bone marrow cells and, in particular, growth and differentiation of hemopoietic and/or accessory cells into functional leukemia cells. For example, the following classical media may be used and supplemented, if desired, with vitamin and amino acid solutions, serum, and/or antibiotics: Fisher's medium (Gibco), Basal Media Eagle (BME), Dulbecco's Modified Eagle Media (D-MEM), Iscoves's Modified Dulbecco's Media, Minimum Essential Media (MEM), McCoy's 5A Media, and RPMI Media.

Specialized media may also be used such as, MyeloCult™ (Stem Cell Technologies) and Opti-Cell™ (ICN Biomedicals). If desired, serum free media may be used such as StemSpan SFEM™ (StemCell Technologies), StemPro 34 SFM (Life Technologies), and Marrow-Gro (Quality Biological Inc.).

In a preferred embodiment, McCoy's 5A medium (Gibco) is used at about 70% v/v, supplemented with vitamin and amino acid solutions. In an even more preferred embodiment, the culture medium comprises approximately 70% (v/v) McCoy's 5A medium (Gibco), approximately $1 \times 10^{-6}$ M hydrocortisone, approximately 50 μg/ml penicillin, approximately 50 mg/ml streptomycin, approximately 0.2 mM L-glutamine, approximately 0.45% sodium bicarbonate, approximately 1× MEM sodium pyruvate, approximately 1× MEM vitamin solution, approximately 0.4×MEM amino acid solution, approximately 12.5% (v/v) heat inactivated horse serum and approximately 12.5% heat inactivated FBS, or autologous serum. The medium chamber may be continuously perfused if desired.

The bioreactor is inoculated with leukemia cells by gently adding e.g., pipetting, into the three-dimensional scaffolding portion of the bioreactor. Alternatively, the leukemia cells may be added to the culture covering and/or surrounding the three dimensional scaffolding. Cells will settle or migrate into the porous or fibrous material making up the scaffolding. The number of cells added to the bioreactor depends on the total area of the three-dimensional scaffolding and volume of culture media. Preferably, leukemia cells isolated from any of the sources discussed extensively herein, are centrifuged through a gradient such as a Ficol/Plaque to remove mature red blood cells, yielding mononuclear cells.

For a bioreactor having a culture chamber of about 3/16" height by about 5/16" width by about 5/16" length and packed with about 0.01 g of a porous or fibrous substrate, the number of mononuclear cells added to the bioreactor may be anywhere in the range of from about $10^4$ to $10^9$ mononuclear cells. Preferably, $4-6 \times 10^6$ cells may be used to inoculate the bioreactor. Using these guidelines, one skilled in the art is able to adjust the number of cells used to inoculate the bioreactor depending on the total area of the three-dimensional scaffolding, volume of culture media, type of three-dimensional scaffolding, and source of leukemia cells.

Preferably, the culture is fed every second day with the culture medium with or without exogenous growth factors. Various other ingredients may be added to the culture media in order to further stimulate leukemia cells growth and differentiation. Thus, for example, cytokines, such as, granulocyte colony stimulating factor, granulocyte monocyte colony stimulating factor, IL3, or IL2 may be added to the culture medium.

The cell culture is allowed to grow anywhere from about a few days to a few weeks. Preferably, the cultures are harvested after about three weeks.

Cells may be harvested in any number of well known methods. The chamber may be treated with any suitable agent, such as collagenase, to release the adhering cells. Non-adhering cells may be collected as they release into the medium. Cells may also be removed from the substrate by physical means such as shaking, agitation, etc. Thereafter, the cells are collected using any known procedure in the art such as, pipetting or centrifugation. Preferably, non-adherent cells are released by gentle stirring and mixing the bed of porous or fibrous material and then collected by centrifugation or sedimentation.

If desired, the cell samples collected from the bioreactor may be further enriched for leukemia cells using well known methods of positive selection. Thus, for example, a solid support (such as beads) having an antibody that binds leukemia cells conjugated thereto, may be mixed with the cell sample. Antibody conjugated beads with leukemia cells bound thereto are then collected by gravity or other means such as a magnet, in the case of magnetic beads.

Negative selection may also be used as a means of enriching the leukemia cells population in the cell sample removed from the bioreactor. With a negative selection scheme, a solid support (such as beads) having conjugated thereto one or more antibodies which react with cells other than leukemia cells may be mixed with the cell sample. Antibody conjugated beads with cells other than leukemia cells bound thereto are then collected by gravity or other means such as a magnet, in the case of magnetic beads.

In either positive or negative selection, the leukemia cells may be further isolated by filtration based on size. In accordance with the present invention, however, the cell samples removed from the bioreactor comprise functional leukemia cells which may be used in many different clinical and drug screening settings without being further enriched.

Leukemia cells may be identified using any of the well known indicia such as abhorrent surface marker staining which is unique to each leukemia type.

The cultured leukemia cells of the present invention have a myriad of uses in the therapeutic and pharmaceutical industries. For example, the subject leukemia cells may be used to screen for drugs and therapeutics (including immunotherapies) which either inhibit or stimulate leukemia cell formation or function.

It is now known that leukemia is associated with overproduction of leukemia cells. For example, leukemia cell formation is a condition whereby a disturbance in the DNA of a previously normal cell of the bone marrow or lymphoid tissues makes cells more prone to proliferation. Thus, inhibitors of leukemia cell formation identified by the assays of the present invention are useful for the treatment of leukemia.

Thus in accordance with the present invention, there are provided methods of screening for drugs which affect leukemia cell formation. As used herein, "drug" or "test compound" encompasses any element, molecule, chemical compound, hormone, growth factor, nucleotide sequence (including oligonucleotides), protein (including peptides), cells, irradiation, and reagents which have the ability to inhibit or stimulate leukemia cell formation and function.

In a typical screening assay for a drug which affects leukemia cell production, cultured leukemia cells are removed from the bioreactor and placed in a petri dish, flask, microscope slide, microtiter dish or the like with enough culture medium or buffered solution to keep the leukemia cells alive. The liquid medium should preferably mimic the blood environment of the body since this is ultimately where the drug which inhibits function will be acting. Preferably, a pH of approximately 7.2, and a temperature of about 37° C. is maintained. The number of leukemia cells which may be used in a screening assay is empirical. Typically, a sample containing $1 \times 10^6$ total cells may be used, depending upon the number of leukemia cells in the cell sample.

The number of leukemia cells in a cell sample relative to other cells may be determined microscopically by counting morphologically leukemic cells or blasts. Immunohistochemical staining, flow cytometry, or a combination thereof may also be performed. Methods of cell counting are well known in the art. The concentration of the test compound—i.e., the drug to be screened as a potential inhibitor of leukemia cell activity is empirical. One skilled in the art is familiar with methods of adjusting concentrations of different compositions in order to best identify the effects of a test compound in the screening assay. Typically, a range of concentrations is used and those portions of the range which exhibit serious deleterious effects on leukemia cell viability are eliminated from further study. Those portions of the range having less deleterious effects on leukemia cell viability are identified and used for further study of inhibitory or stimulatory effects on leukemia formation, leukemia activity, or leukemia cells functionality.

The mixture of leukemia cells and test compound is incubated for a time and under conditions sufficient for the inhibition or stimulation of leukemia cell activity to be carried out. As defined herein, a sufficient time can be anywhere from about five minutes to several hours or more. When leukemia cells are tested in a petri dish, flask, microscope slide, microtiter dish, or the like, a sufficient time may be several minutes to several hours. Of course, the test time may be extended if needed in order to see effects on the cells. The skilled artisan is able to determine the optimal time for running the screening assay by removing samples and examining cells microscopically for viability.

A preferred buffer for use in the reactions is Phenol red-free MEM supplemented with 1× nonessential amino acids, 1× L-glutamine, 10% FBS, 50 U/ml penicillin, and 50 µg/ml streptomycin. In a preferred embodiment, the test reaction volume is between about 0.5 and about 2 ml. In a more preferred embodiment, the reaction volume is about 1 ml. In a preferred embodiment, the incubation temperature is approximately 37° C.

In an alternative embodiment, there is provided a method for screening for drugs which either inhibit or stimulate leukemia cell formation. In this embodiment, a test compound is added directly to the bioreactor. The test compound may be added to the culture medium or into the three dimensional scaffolding. The time at which the test compound is added is empirical but is relatively early. Typically, control runs are performed in which no test compounds are added to the bioreactor.

The ability of a test compound to inhibit leukemia cell formation may be determined by leukemia cell count, immunohistochemical staining, flow cytometry, or a combination thereof. Methods of cell counting are well known in the art. Cell counts are compared between experimental and control assays. Increased numbers of leukemia cells compared to control runs correlate with the identification of a stimulator of leukemia cell formation. Decreased numbers of leukemia cells compared to control runs correlate with the identification of an inhibitor of leukemia cell formation.

As described above, however, any available test compound may be used to screen for effective inhibitors of leukemia cell formation, activity, or functionality.

In one aspect of the present invention the leukemia cells are isolated from a leukemia patient and, then, subjected to the cell culturing process of the present invention. The test compound is then used to treat such cultured cells in order to determine which compound is particularly effective in treating the patient's leukemia. Based on this test procedure, the most effective test compound is administered to the patient to inhibit growth of leukemia cells in the leukemia patient.

The present invention provides the means of sustaining a patient's leukemic cells in culture in order to provide leukemic antigens for immunotherapy purposes. Examples of this include donor lymphocyte infusions and dendritic cells therapies.

The present invention also provides a method for identifying genes which are related to in leukemia cell formation or function. In this aspect of the invention, various parameters of the culture conditions may be changed (e.g., nutrient ingredients (including leukemia cell agents, temperature, oxygen concentration, $CO_2$ concentration, and nutrient composition), cytokine environment, cellular content, and inhibition of receptors, signaling, or adhesion molecules. After altering one or more parameters, leukemia cell number and function is determined. The leukemia cell number may be determined by morphological, immunohistochemical, or flow cytometric techniques. If changes in leukemia cell number and function occur in a test sample when compared to a control sample, then the system may be used to further screen for the gene or genes accountable for the change. Differential gene display, its modified versions such as RNA arbitrarily primed (RAP)-PCR technique or gene microarray analysis, may be used to further identify and characterize the genes involved. These methods are well known in the art. Alternatively, comparison with a 2-dimensional Dexter culture which does not support leukemia cells can be used to screen for genes. Furthermore, the genes associated with the leukemia cells of the test sample may be identified by cloning the genes expressed by the purified or enriched subject leukemia cells.

The invention is further illustrated by the following specific examples which are not intended in any way to limit the scope of the invention.

EXAMPLES

Example 1

Preparation of the Bioreactor

The bioreactor was fabricated using polycarbonate plates (FIG. 1A). The culture chamber (3/16" H×5/16" W×5/16" L) was packed with 0.01 g of th highly porous microcarrier. The packed-bed of microcarriers was overlayered with culture medium. The medium chamber (1/2" H×5/16" W×12/16" L) contained 0.6 ml of medium. A Teflon™ membrane (50 µm thickness) was used to facilitate gas exchange.

Figure 1B:
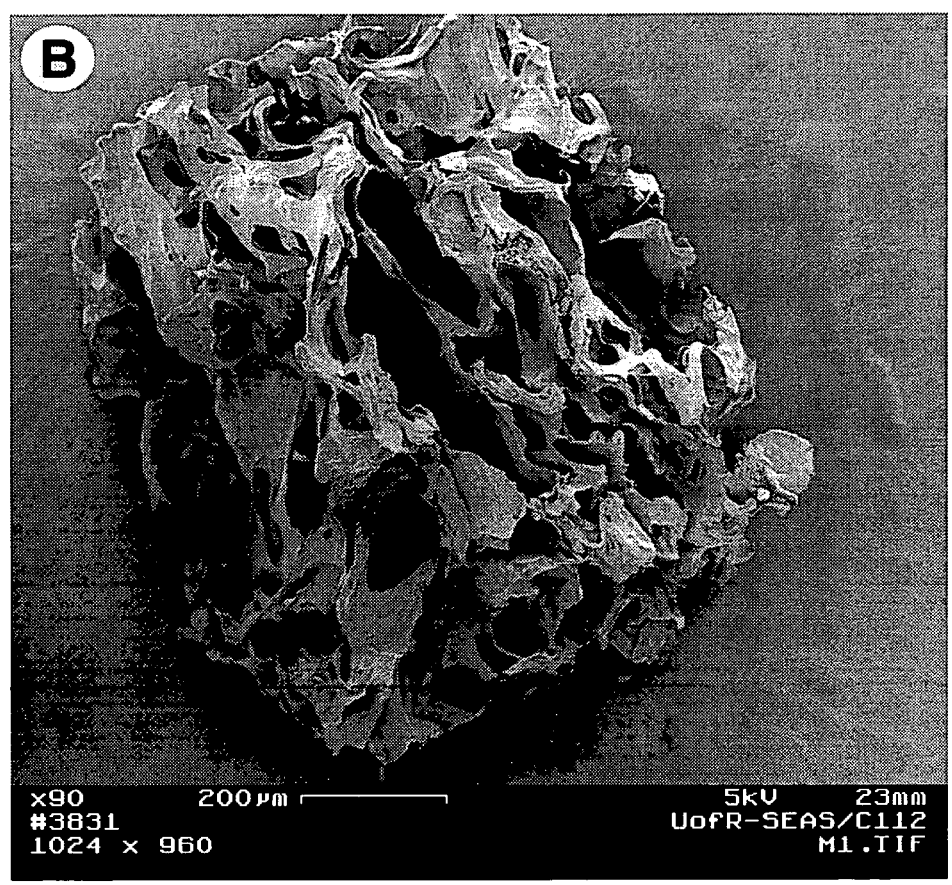
FIG. 1B is a scanning electron micrograph of a macroporous cellulose microsphere used as artificial scaffolding in the bioreactor.

Cellsnow™—EX, type L (low ion-charged), macroporous cellulose microcarriers (Kirin, Japan; 1–2 mm diameter; 100–200 µm pore size; 95% porosity) were used throughout these experiments as an artificial scaffolding for the human bone marrow cells (FIG. 1B).

Example 2

Human Bone Marrow Preparation

Bone marrow, aspirated from the iliac crest of consenting donors according to the instructions from the University of Rochester's Research Subjects Review Board, was diluted 1:1 with McCoy's 5A medium (Gibco, Grand Island, N.Y.), overlayered onto Ficol/Paque (Pharmacia, Piscataway, N.J., density 1.027 g/ml), and centrifuged at 200 g for 30 minutes. The mononuclear cell layer was collected, washed 3 times, and used to inoculate the bioreactor. A portion of the cells was set aside to be used in various assays as needed.

Example 3

Three-Dimensional Human Long-Term Bone Marrow Culture

The cultures were inoculated with the proper number of mononuclear cells ($4$–$6 \times 10^6$ cells per culture chamber) by pipetting into the porous microcarrier section of the bioreactor. The cultures were incubated in a humidified $CO_2$ incubator (containing 5% $CO_2$) at 37° C. The LTBMC medium (changed daily) consisted of 70% (v/v) McCoy's 5A medium (Gibco), $1 \times 10^{-6}$ M hydrocortisone (Sigma, St. Louis, Mo.), 50 µ/ml penicillin (Sigma), 50 mg/ml streptomycin (Sigma), 0.2 mM L-glutamine (Gibco), 0.045% sodium bicarbonate (Sigma), 1×MEM sodium pyruvate (Gibco), 1×MEM vitamin solution (Gibco), 0.4×MEM amino acid solution (Gibco), 12.5% (v/v) heat inactivated horse serum (Gibco), and 12.5% heat inactivated FBS (Gibco). For the first 2 weeks, the cultures were fed every second day with the complete culture medium. At week 2, the cultures were depopulated by gently stirring and mixing the bed of porous microspheres to release the non-adherent cells (50 µl/well). Viable cell count for the nonadherent cells was determined by the dye-exclusion method using Trypan blue dye (Sigma) and a hemocytometer. The cultures were harvested weekly by gentle pipetting and sacrificed between weeks 4 and 5 to perform the various assays.

Example 4

Differential Cell Analysis

Cytospin slides of the nonadherent cells obtained from the human bone marrow cells were prepared by centrifugation of 20,000 cells/slide in cytospin funnels at 500 rpm for 5 min using a cytospin centrifuge (Shandon, Sewickly, Pa.). The cells were air-dried prior to staining with Wright's stain (Geometric Data, Wayne, Pa.) for 15 min., followed by a distilled water wash for 1 min. Differential cell count was performed blindly by counting over 100 cells per sample. For each culture condition, six to nine identical cultures were established. Lefkovits, I., ed. *Immunology Methods Mannual: The Comprehensive Sourcebook of Techniques*, Academic Press, San Diego (1997), which is hereby incorporated by reference.

Example 5

Cell Morphology Characterization

The scaffolding and the cells within it were removed from the bioreactor and embedded in 2% Bacto agar (Gibco). They were then fixed in 10% neutral buffered formalin (Fisher, Pittsburgh, Pa.) for at least one hour. The scaffolding and cells were then infiltrated with paraffin. Humason, G. L., *Animal Tissue Techniques*, W. H. Freeman and Company, San Fransisco (1967), which is hereby incorporated by reference. Paraffin thin-sections of the three-dimensional bone marrow cells were serially cut at 4–5 µm thickness and mounted on chemically coated slides. The paraffin thin-sections were deparaffinized with xylene, 100% alcohol, 95% alcohol, and 70% alcohol followed by a rinse with tap water. The thin-sections were then stained with Mayers hematoxylin-eosin and microscopically examined in order to characterize cell morphology.

Example 6

Chronic Lymphocytic Leukemia Cells

Figure 2:
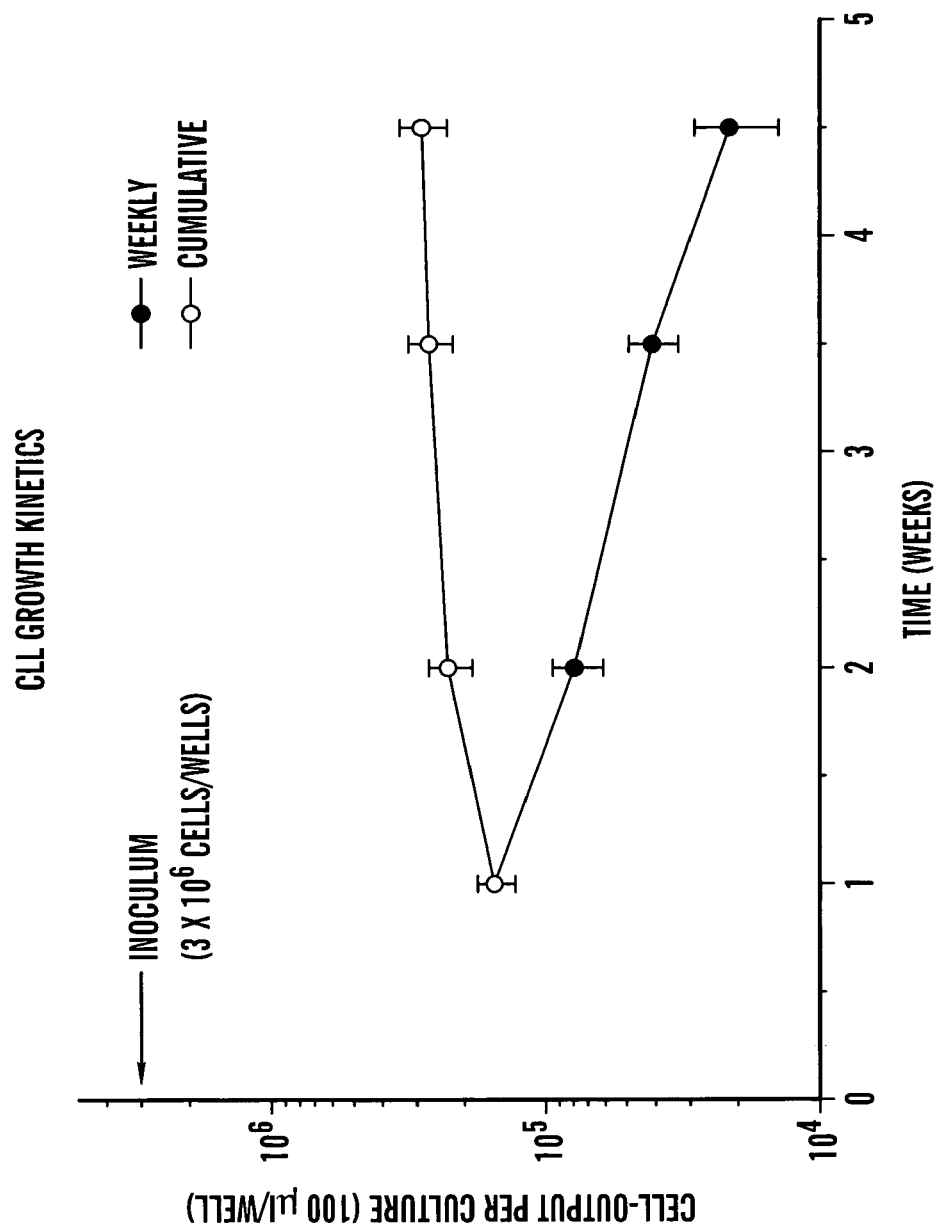
FIG. 2 shows chronic lymphocytic leukemia ("CLL") growth kinetics in the form of a graph of cell-output per culture (100 µl/well) v. time (weeks).
Figure 3:
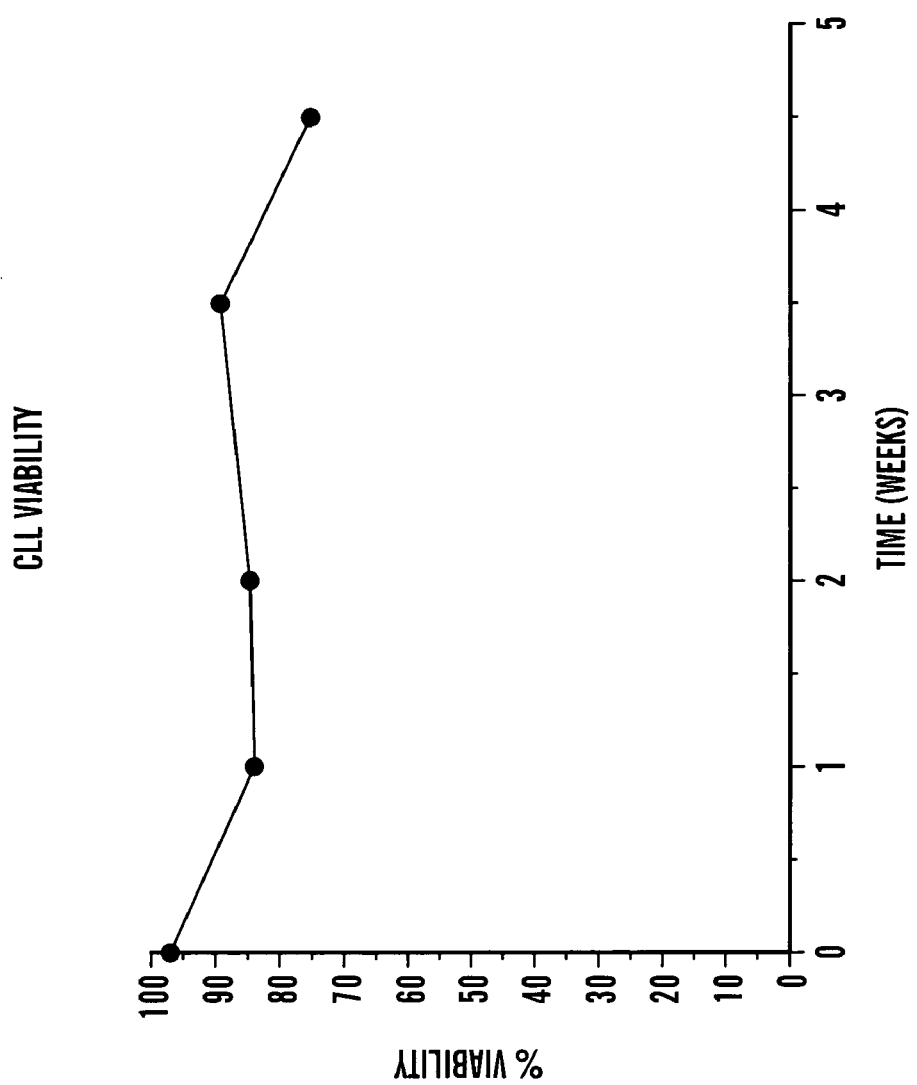
FIG. 3 shows CLL viability in the form of a graph of % viability of CLL v. time (weeks).
Figure 4:
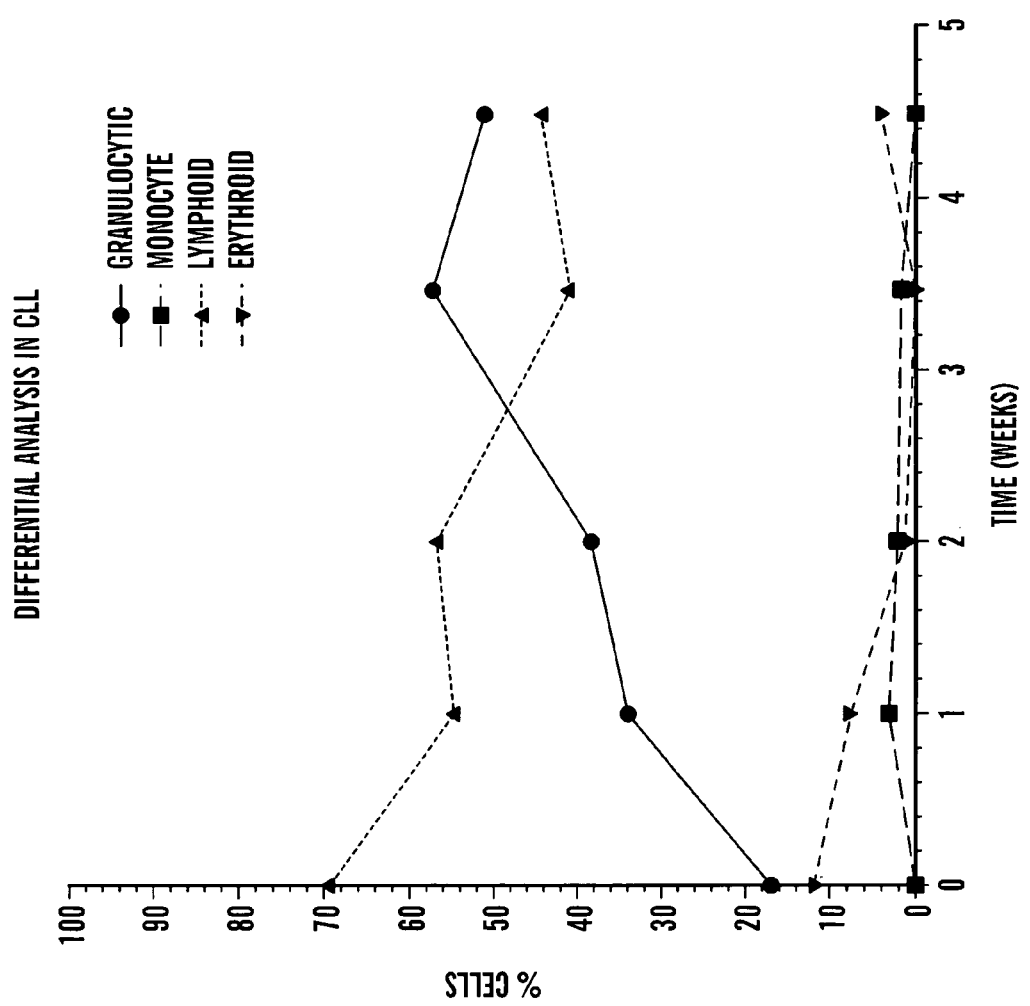
FIG. 4 shows the differential analysis in CLL in the form of a graph of % of cells v. time (weeks).

Mononuclear cells from an individual with chronic lymphocytic leukemia were isolated and placed in a bioreactor in accordance with Examples 1–3. In the absence of exogenous growth factors, these cells were maintained in the cell-output. FIG. 2 demonstrates the observed cell output (weekly and cumulatively). The viability of the cell-output was maintained above 75% throughout the culture period, as demonstrated in FIG. 3. Differential cell analysis indicated the maintenance of the lymphocytic cell population after the initial decline at week 1 (FIG. 4). Furthermore, a malignant lymphoid module was observed in paraffin thin sections from the bioreactor culture sacrificed at week 4.5 similar to what was observed in this individual's bone marrow biopsy. Extensive stroma cell development was observed in the paraffin thin-sections from the culture.

Example 7

Acute Myelocytic Leukemia Cells

Figure 5:
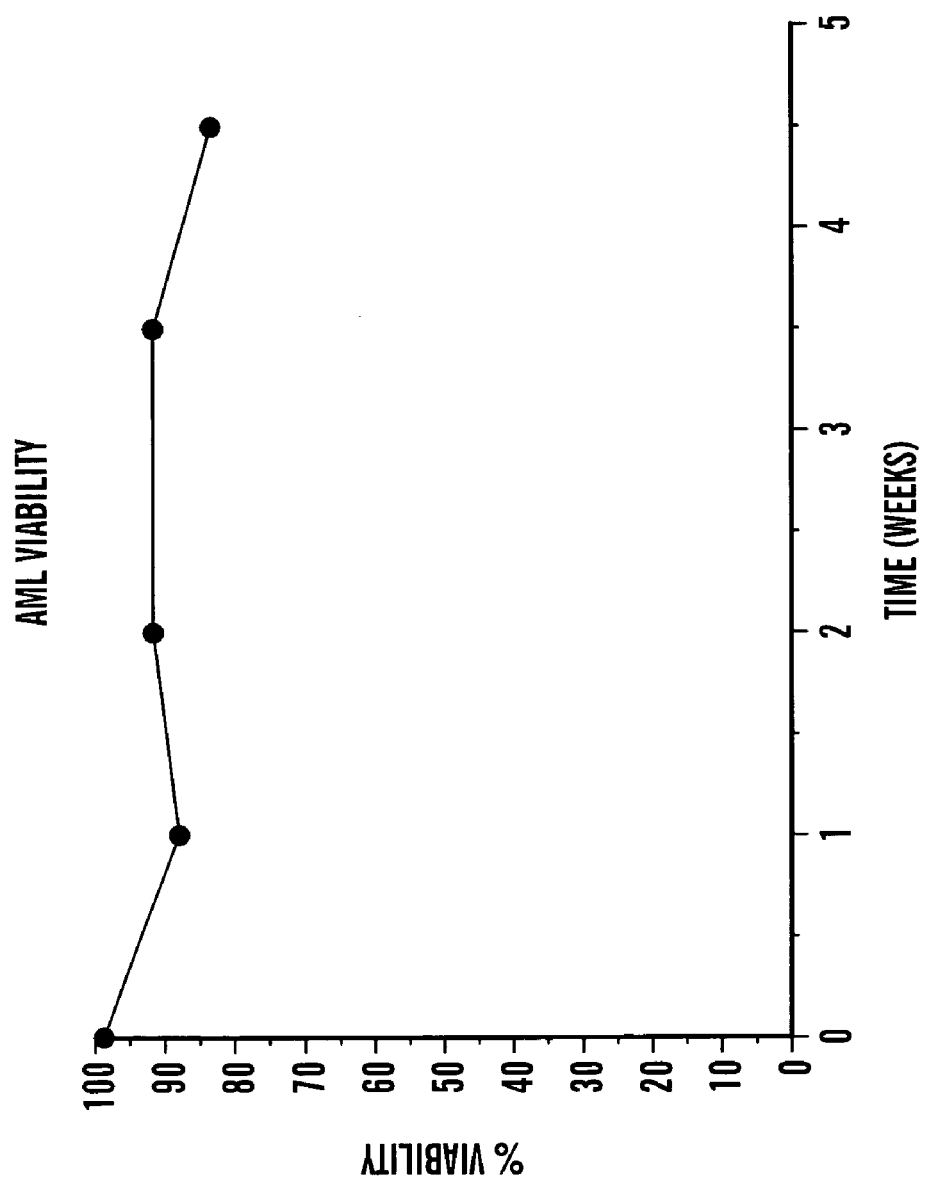
FIG. 5 shows the viability of acute myelocytic leukemia cells ("AML") in the form of % viability of AML v. time (weeks).
Figure 6:
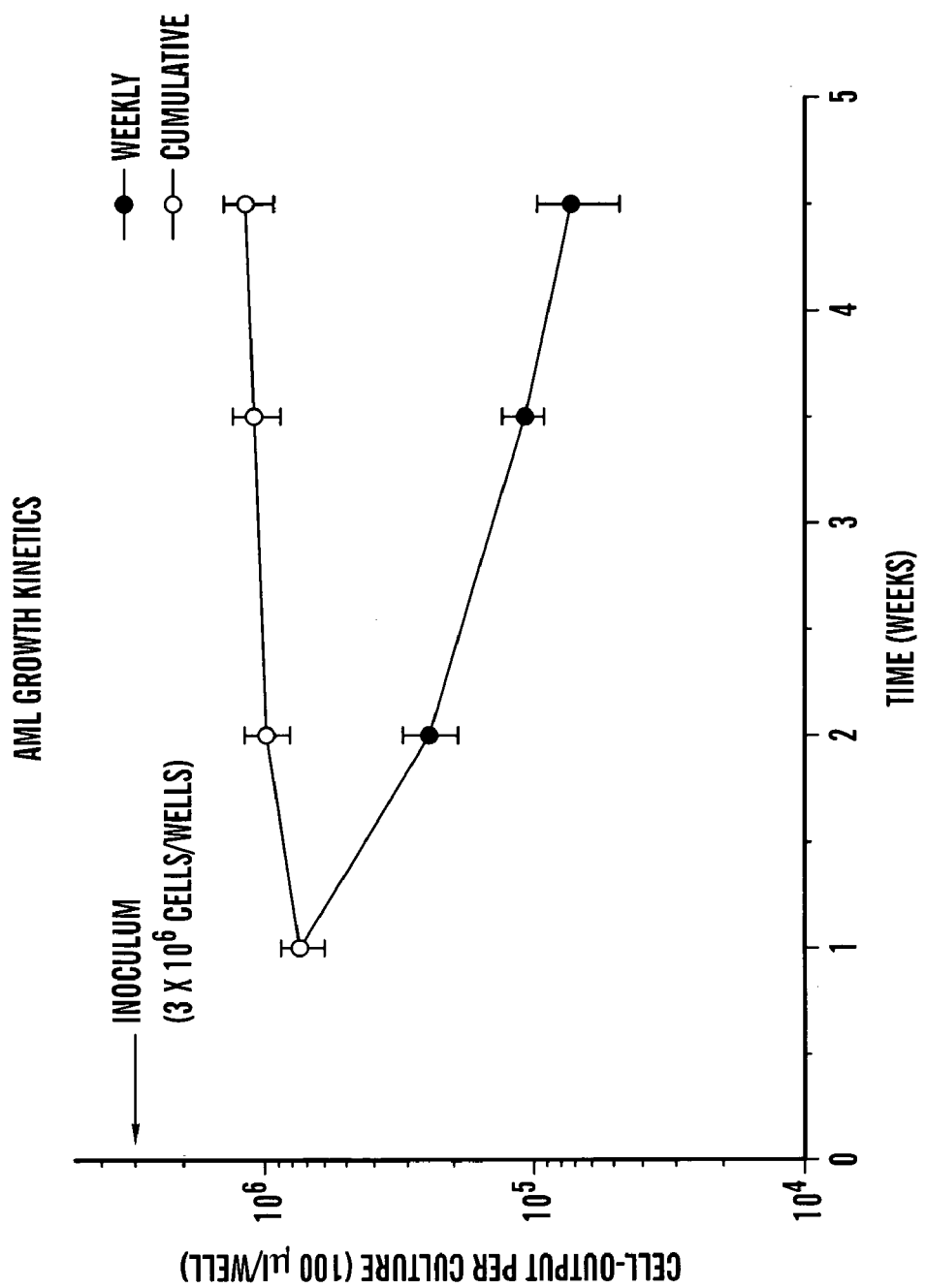
FIG. 6 shows the AML growth kinetics in the form of a graph of cell-output per culture (100 µl/well) v. time (weeks).
Figure 7:
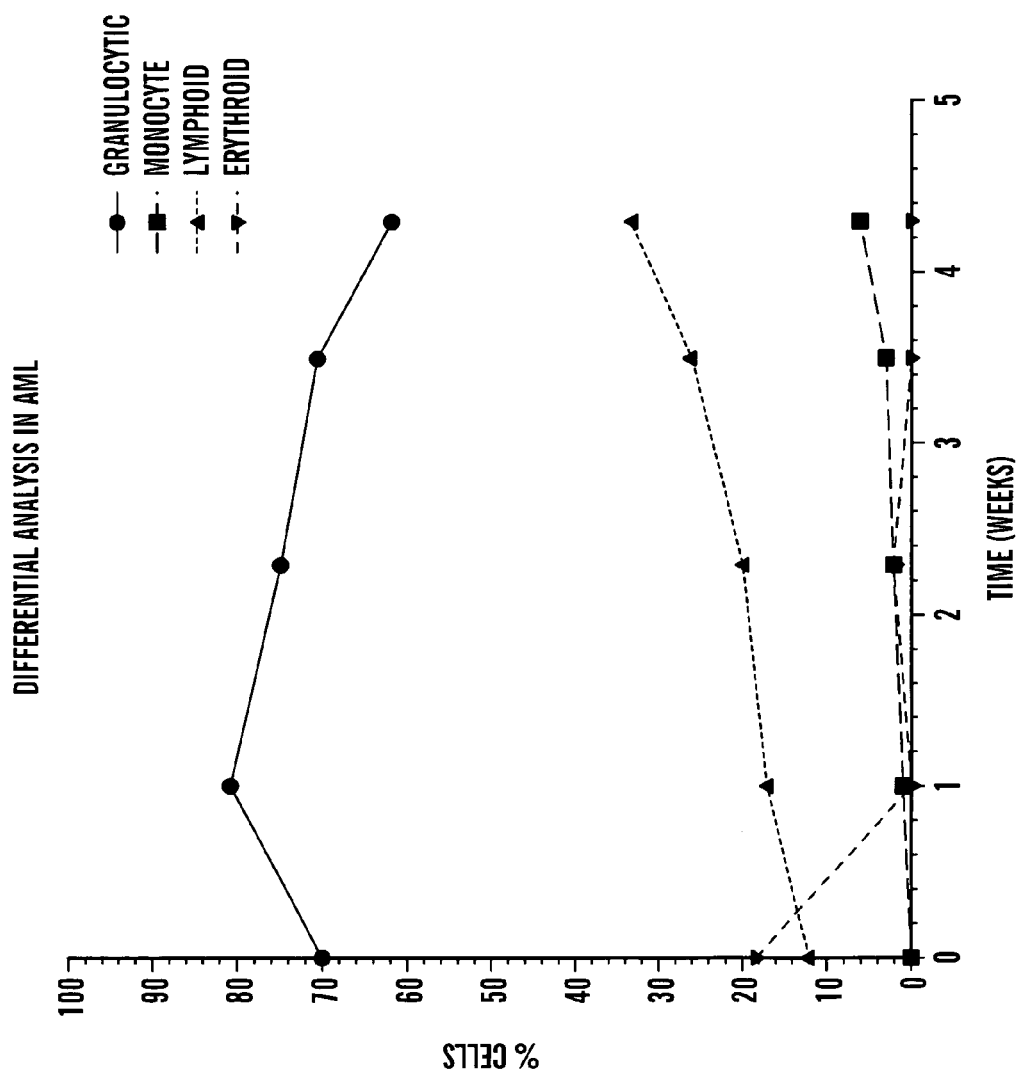
FIG. 7 shows the differential analysis in AML in the form of a graph of % of cells v. time (weeks).
Figure 8:
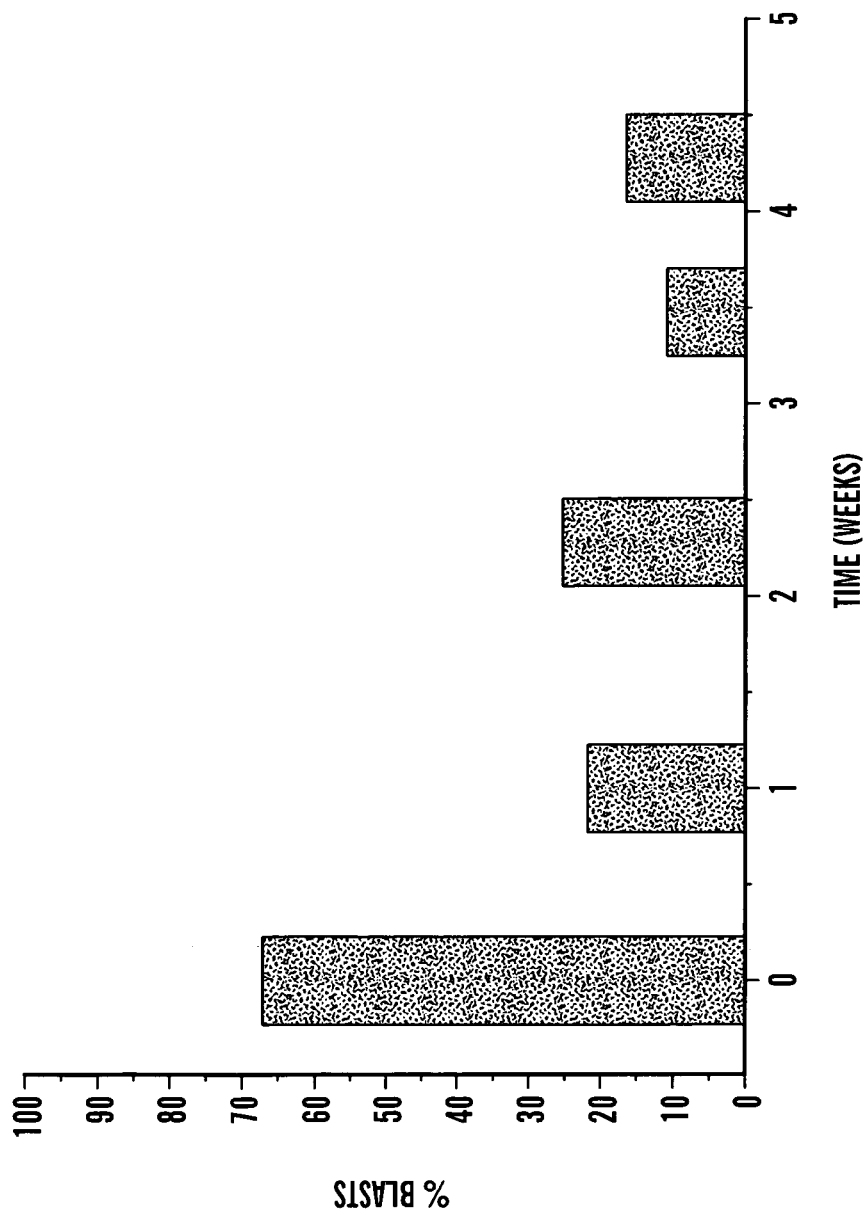
FIG. 8 shows the AML blast kinetics in the form of a bar chart of the % of blasts v. time (weeks).
Figure 9A:
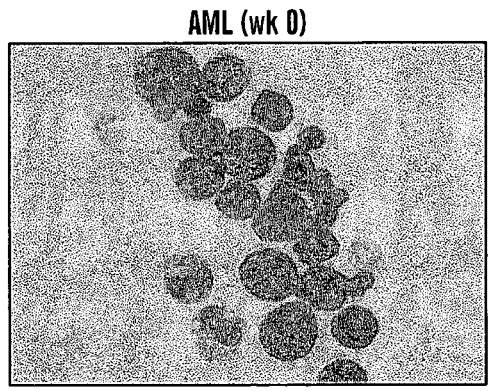
FIGS. 9A–E show AML at week 0 (i.e. before being cultured in the bioreactor of the present invention).
Figure 9B:
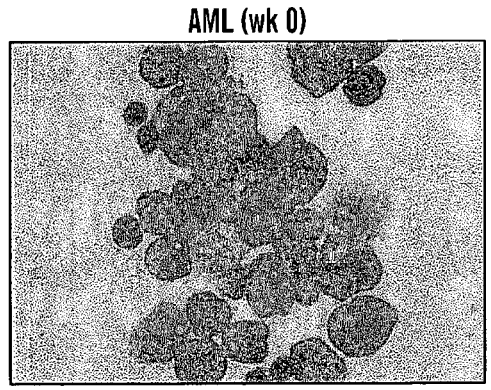
Figure 9C:
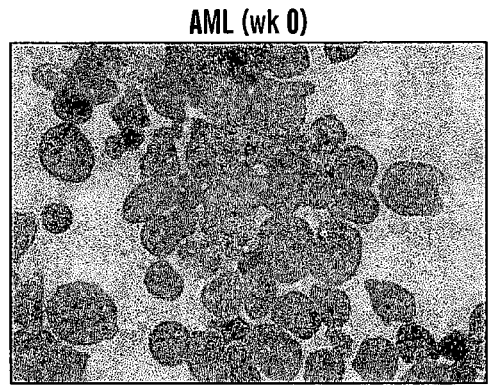
Figure 9D:
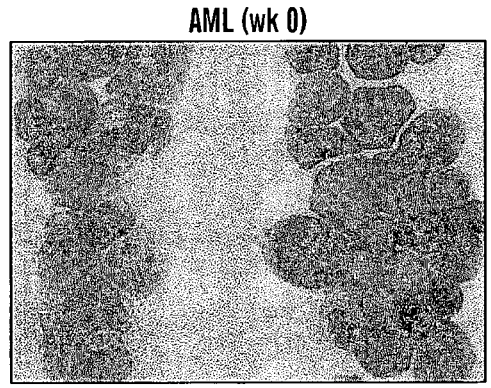
Figure 9E:
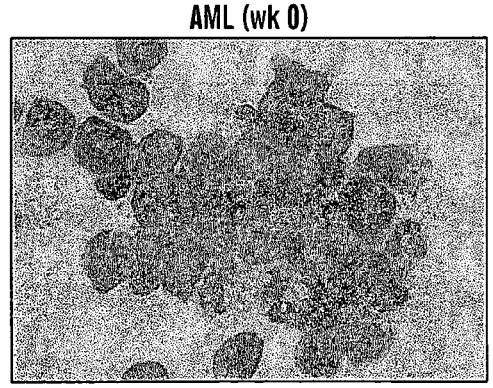
Figure 10A:
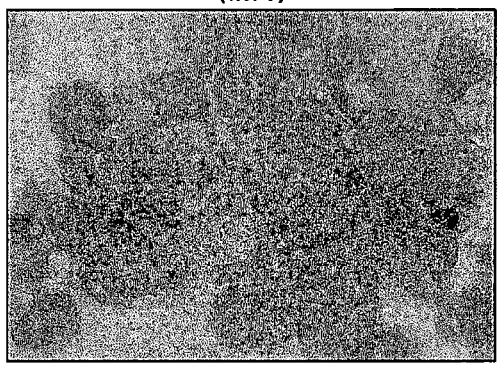
FIGS. 10A–D show AML after 1 week (i.e. week 1) of being cultured in the bioreactor of the present invention.
Figure 10B:
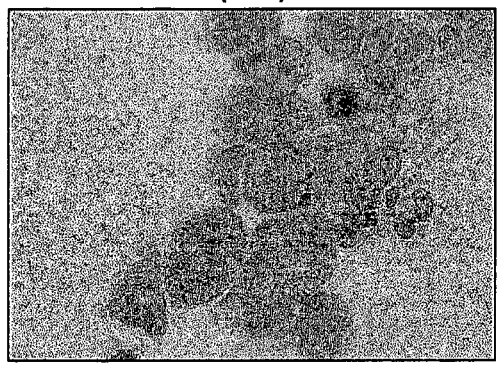
Figure 10C:
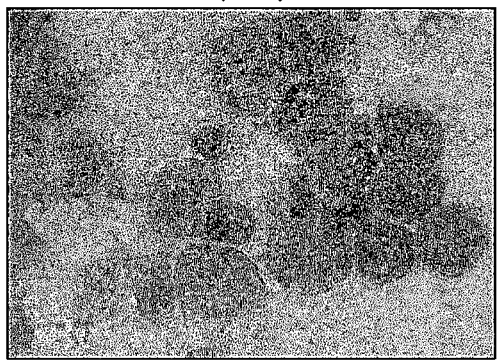
Figure 10D:
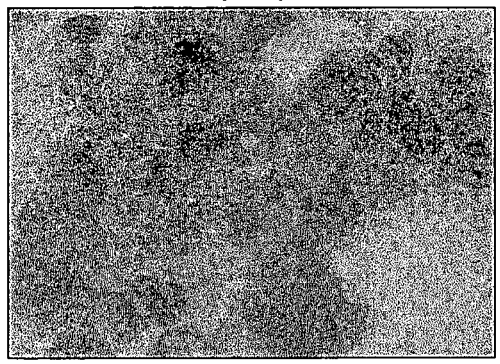
Figure 11A:
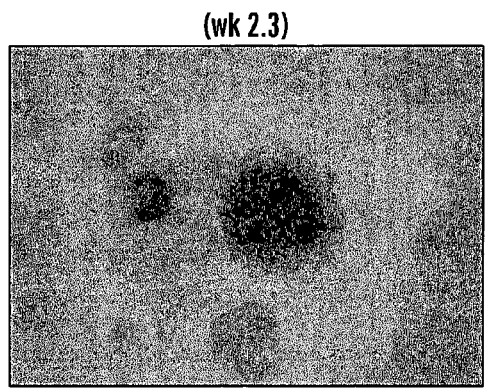
FIGS. 11A–D show AML after 2.3 weeks (i.e. week 2.3) of being cultured in the bioreactor of the present invention.
Figure 11B:
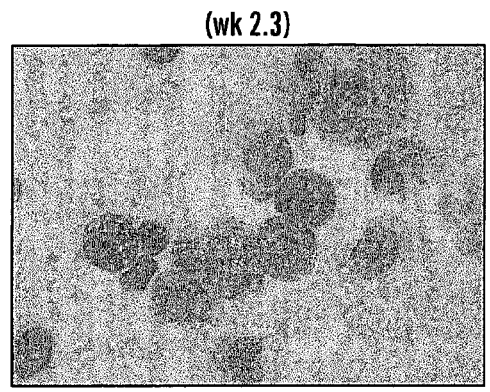
Figure 11C:
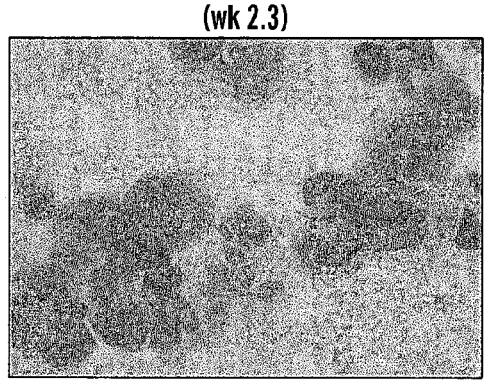
Figure 11D:
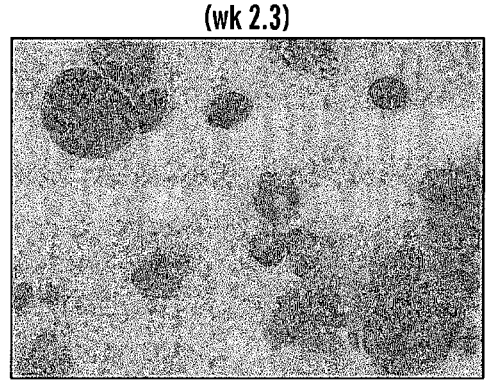
Figure 12A:
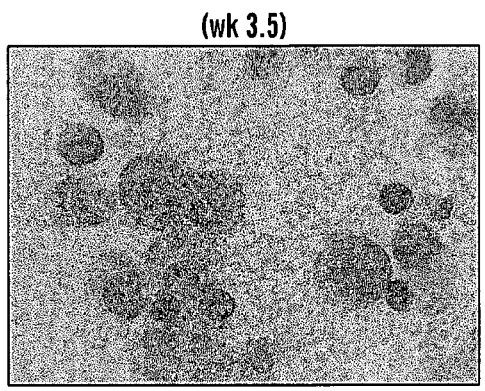
FIGS. 12A–D show AML after 3.5 weeks (i.e. week 3.5) of being cultured in the bioreactor of the present invention.
Figure 12B:
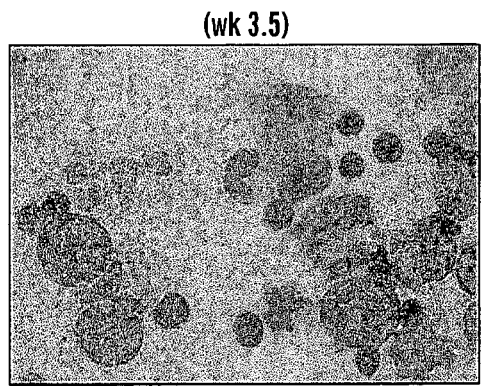
Figure 12C:
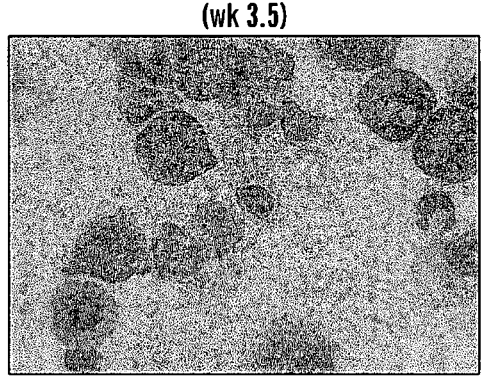
Figure 12D:
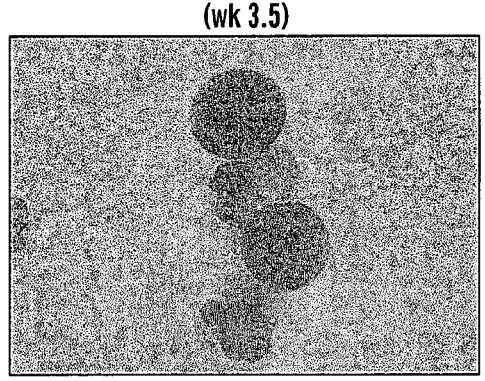
Figure 13A:
FIGS. 13A–E show AML after 4.3 weeks (i.e. week 4.3) of being cultured in the bioreactor of the present invention.
Figure 13B:
Figure 13C:
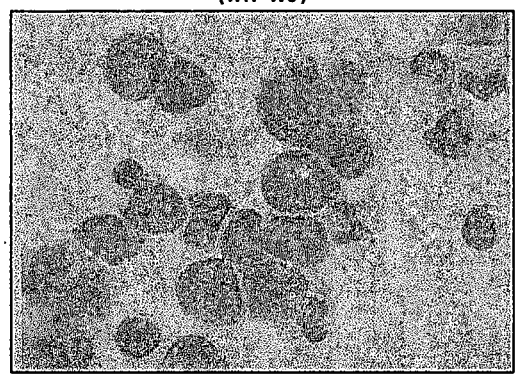
Figure 13D:
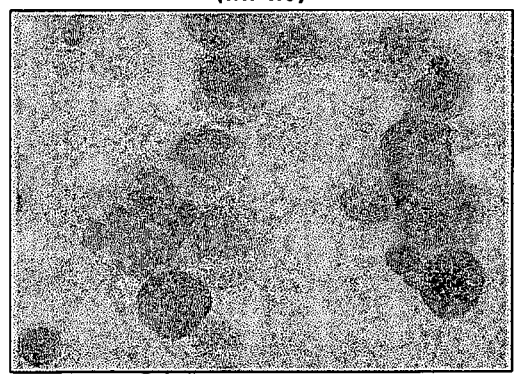
Figure 13E:
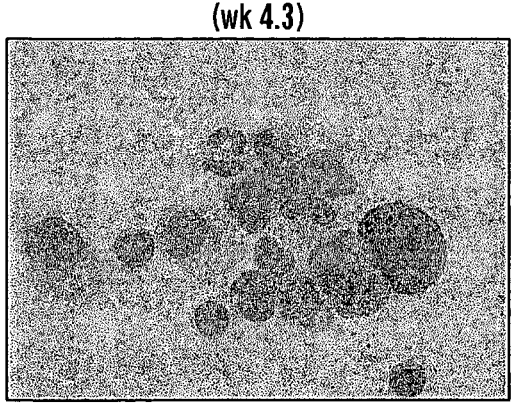

Mononuclear cells from an individual with acute myelocytic leukemia were isolated and placed in a bioreactor in accordance with Examples 1–3. In the absence of exogenous growth factors, these cells were maintained in the three-dimensional bioreactor, as illustrated by the bioreactor cell-output kinetics shown in FIG. 6. The viability of the cell-output was maintained above 80–85% throughout the culture period, as shown in FIG. 5. Differential cell analysis kinetics indicated the maintenance of the granulocytic cell population throughout the culture (FIG. 7). Myeloid leukemic blasts were present throughout the culture period after an initial decline during week 1, as shown in FIG. 8. The acute myelocytic leukemia cell culture was actively proliferating, as demonstrated by the presence of mitotic blasts throughout the culture period. FIG. 9 shows a cytospin preparation at week 0 prior to the inoculation of the culture. A leukemic blast can be identified based on a high nuclear to cytoplasmic ratio and the presence of nucleoli. FIGS. 10 and 11 show a cytospin preparation after 1 and 2 weeks of culture, respectively. Persistence of the leukemic blasts is noted. FIGS. 12 and 13 show a cytospin preparation after 3.5 and 4.3 weeks of culture. Actively dividing cells are present in the bioreactor cultures as indicated by the mitotic figures. Furthermore, the persistence of leukemic blasts is also evident.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of culturing leukemia cells, comprising:
   isolating mononuclear cells, which contain leukemia cells, from a subject and
   culturing the cells in a chamber having a scaffolding covered or surrounded with culture medium, wherein said scaffolding allows for leukemia cells to have cell to cell contacts in three dimensions, and the leukemia cells are cultured for a duration of at least four weeks.

2. The method according to claim 1, wherein the leukemia cells are mammalian leukemia cells.

3. The method according to claim 2, wherein the mammalian leukemia cells are human leukemia cells.

4. The method according to claim 1, wherein the leukemia cells are acute myelocytic cells.

5. The method according to claim 1, wherein the leukemia cells are chronic lymphocytic leukemia cells.

6. The method according to claim 1, wherein the scaffolding is selected from the group consisting of tangled fibers, porous particles, sponge, sponge-like material, and combinations thereof.

7. The method according to claim 1, wherein the scaffolding is formed from a material selected from the group consisting of metal, glass, ceramic, plastic, hydroxyapatite, treated or untreated bone, a synthetic polymer, a natural substance, a semisynthetic material, and combinations thereof.

8. The method according to claim 7, wherein the material is degradable.

9. The method according to claim 7, wherein the material is non-degradable.

10. The method according to claim 1, wherein the culture medium comprises exogenous growth factors.

11. The method according to claim 1, wherein the culture medium includes granulocyte colony stimulating factor, granulocyte monocyte colony stimulating factor, IL3, or IL2.

12. The method according to claim 1 further comprising: reseeding the chamber with mononuclear cells.

13. The method according to claim 1, wherein the mononuclear cells are from peripheral blood, bone marrow aspirate or biopsy, chloroma, or spleen.

14. A method of culturing leukemia cells, comprising:
    isolating mononuclear cells, which contain leukemia cells, from a subject and
    culturing the cells in a chamber having a scaffolding covered or surrounded with culture medium, wherein said scaffolding is selected from the group of materials consisting of tangled fibers, porous particles, sponge, sponge-like material, and combinations thereof, wherein the leukemia cells must be able to enter into openings of the fibrous or porous materials, and the scaffolding allows for leukemia cells to have cell to cell contacts in three dimensions.

15. The method according to claim 14, wherein the leukemia cells are mammalian leukemia cells.

16. The method according to claim 15, wherein the mammalian leukemia cells are human leukemia cells.

17. The method according to claim 14, wherein the leukemia cells are acute myelocytic cells.

18. The method according to claim 14, wherein the leukemia cells are chronic lymphocytic leukemia cells.

19. The method according to claim 14, wherein the culture medium comprises exogenous growth factors.

20. The method according to claim 14, wherein the culture medium includes granulocyte colony stimulating factor, granulocyte monocyte colony stimulating factor, IL3, or IL2.

21. The method according to claim 14, further comprising:
    reseeding the chamber with mononuclear cells.

22. The method according to claim 14, wherein the mononuclear cells are from peripheral blood, bone marrow aspirate or biopsy, chloroma, or spleen.

23. A method of culturing leukemia cells, comprising:
    isolating mononuclear cells, which contain leukemia cells, from a subject and
    culturing the cells in a chamber having a scaffolding covered or surrounded with culture medium, wherein said scaffolding is formed from a material selected from the group consisting of metal, glass, ceramic, plastic, hydroxyapatite, a synthetic polymer, a semisynthetic material, and combinations thereof, and the scaffolding allows for leukemia cells to have cell to cell contacts in three dimensions.

24. The method according to claim 23, wherein the material is degradable.

25. The method according to claim 23, wherein the material is non-degradable.

26. The method according to claim 23, wherein the leukemia cells are mammalian leukemia cells.

27. The method according to claim 24, wherein the mammalian leukemia cells are human leukemia cells.

28. The method according to claim 23, wherein the leukemia cells are acute myelocytic cells.

29. The method according to claim 23, wherein the leukemia cells are chronic lymphocytic leukemia cells.

30. The method according to claim 23, wherein the culture medium comprises exogenous growth factors.

31. The method according to claim 23, wherein the culture medium includes granulocyte colony stimulating factor, granulocyte monocyte colony stimulating factor, IL3, or IL2.

32. The method according to claim 23 further comprising:
    reseeding the chamber with mononuclear cells.

33. The method according to claim 23, wherein the mononuclear cells are from peripheral blood, bone marrow aspirate or biopsy, chloroma, or spleen.

* * * * *